United States Patent
Chen

(10) Patent No.: US 6,548,088 B1
(45) Date of Patent: Apr. 15, 2003

(54) MEDICINAL PREPARATION FOR DISINFECTING VAGINAS

(76) Inventor: Bih Cheng Chen, No. 118, Chong San Road, Taichung (TW), 400

( * ) Notice: Subject to any disclaimer, the term of this patent is extended or adjusted under 35 U.S.C. 154(b) by 0 days.

(21) Appl. No.: 10/161,175

(22) Filed: Jun. 4, 2002

(51) Int. Cl.[7] .......................... A61K 35/78; A01N 65/00
(52) U.S. Cl. ....................... 424/728; 424/725; 424/741; 424/773; 424/777
(58) Field of Search ................................. 424/728, 725, 424/773, 777, 741

(56) References Cited

U.S. PATENT DOCUMENTS 6,242,012 B1 * 6/2001 Newmark et al. ........... 424/773

OTHER PUBLICATIONS

Computer DWPI Abstract 2001–356733 Yu, CN 1287855 Mar. 2001.*
Computer JPAB Abstract Tomono et al JP411279069 Oct. 1999.*
Computer DWPI Abstract 1987–084173 Nitto Electric JP 62036328 Feb. 1987.*

* cited by examiner

*Primary Examiner*—Herbert J. Lilling
(74) *Attorney, Agent, or Firm*—Charles E. Baxley

(57) ABSTRACT

A medicinal preparation includes a number of medicinal materials having *asari radix, fructus cnidii, nelumbo nucifera gaertner, ginseng radix, angelica sinensis radix, scutellaria baicalensis, phellodendron amurense radix, evodiae fructus,* and *saussureae radix*, and grounded into powder, and blended with water to form a pasty material which may be refrigerated and dried to form a crystallized material. A number of substrates may then be mixed with the pasty material or the crystallized material, and rotated to form a gluey material for being used by the users.

9 Claims, 1 Drawing Sheet

MEDICINAL PREPARATION FOR DISINFECTING VAGINAS

BACKGROUND OF THE INVENTION

1. Field of the Invention

The present invention relates to a medicinal preparation, and more particularly to a medicinal preparation for cleaning and disinfecting and moistening and tightening the vaginas of women.

2. Description of the Prior Art

Typically, the vaginas of women may have flaccid muscles, or the mucous membranes of the vaginas may become thinner and weak or fragile, or women may feel dry and scorching hot in the vaginas, particularly after childbirth, sexual intercourse, or when women have endocrine disorders. In addition, due to personal hygienic problems, or owing to the infection by germs or bacteria, the vaginas of women may have bad odors, inflammation, leucorrhoea, or the women may feel itchy in the vaginas, and thus may loss sexuality. Various kinds of medicinal preparations have been developed for cleaning the vaginas, for disinfecting the vaginas, for moistening the vaginas, or for tightening the vaginas separately. However, the medicinal preparations may not be used for cleaning and disinfecting and moistening and tightening the vaginas of women simultaneously.

The present invention has arisen to mitigate and/or obviate the afore-described disadvantages of the conventional medicinal preparations.

SUMMARY OF THE INVENTION

The primary objective of the present invention is to provide a medicinal preparation for tightening the vaginas of women, or for increasing or recovering the resilience of the muscles of the vaginas of the women.

The other objective of the present invention is to provide a medicinal preparation for disinfecting the vaginas and to remove the bad odors, inflammation, leucorrhoea or the like from the vaginas of women.

The further objective of the present invention is to provide a medicinal preparation for cleaning and moistening the vaginas of women, for avoiding the vaginas infectious problems.

In accordance with one aspect of the invention, there is provided a medicinal preparation comprising a plurality of medicinal materials including *asari radix, fructus cnidii, nelumbo nucifera gaertner, ginseng radix, angelica sinensis radix, scutellaria baicalensis, phellodendron amurense radix, evodiae fructus*, and *saussureae radix*, the medicinal materials being grounded into powder, and water blending with the powder of the medicinal materials to form a pasty material, in order to clean or to moisten or tighten the vaginas of women, or to increase or recover the resilience of the muscles of the vaginas of the women, or to disinfect the vaginas of women, to remove the bad odors, inflammation, leucorrhoea or the like from the vaginas of women, or to clean and the vaginas of women, or to avoid the vaginas infectious problems.

The *asari radix* includes 10–30% by weight, the *fructus cnidii* includes 10–30% by weight, the *nelumbo nucifera gaertner* includes 5–10% by weight, the *ginseng radix* includes 3–5% by weight, the *angelica sinensis radix* includes 5–10% by weight, the *scutellaria baicalensis* includes 5–10% by weight, the *phellodendron amurense radix* includes 5–10% by weight, the *evodiae fructus* includes 10–30% by weight, and the *saussureae radix* includes 10–30% by weight.

The pasty material may be refrigerated and dried to remove water from the pasty material and to refrigerate the pasty material to a crystallized material.

A plurality of substrates may then be mixed with the pasty material or with the crystallized material, the substrates include papaya enzyme, aloe jelly, bulbus lihii, glycerine, almond oil, ginsengperfume, fatty acid, lactic acid, carbomer, and water material.

The papaya enzyme includes 10% by weight, the aloe jelly includes 10% by weight, the bulbus lilii includes 0.5% by weight, the glycerine includes 15% by weight, the almond oil includes 15% by weight, the ginsengperfume includes 0.5% by weight, the fatty acid includes 5% by weight, the lactic acid includes 0.1% by weight, the carbomer includes 20% by weight, and the water material includes 23.9% by weight.

The substrates and the pasty material may then be rotated with a rotational speed of 1500 rps for about 20 minutes and for well mixing the substrates and the pasty material to form a gluey material.

Further objectives and advantages of the present invention will become apparent from a careful reading of a detailed description provided hereinbelow, with appropriate reference to accompanying drawings.

DETAILED DESCRIPTION OF THE PREFERRED EMBODIMENT

Figure 1:
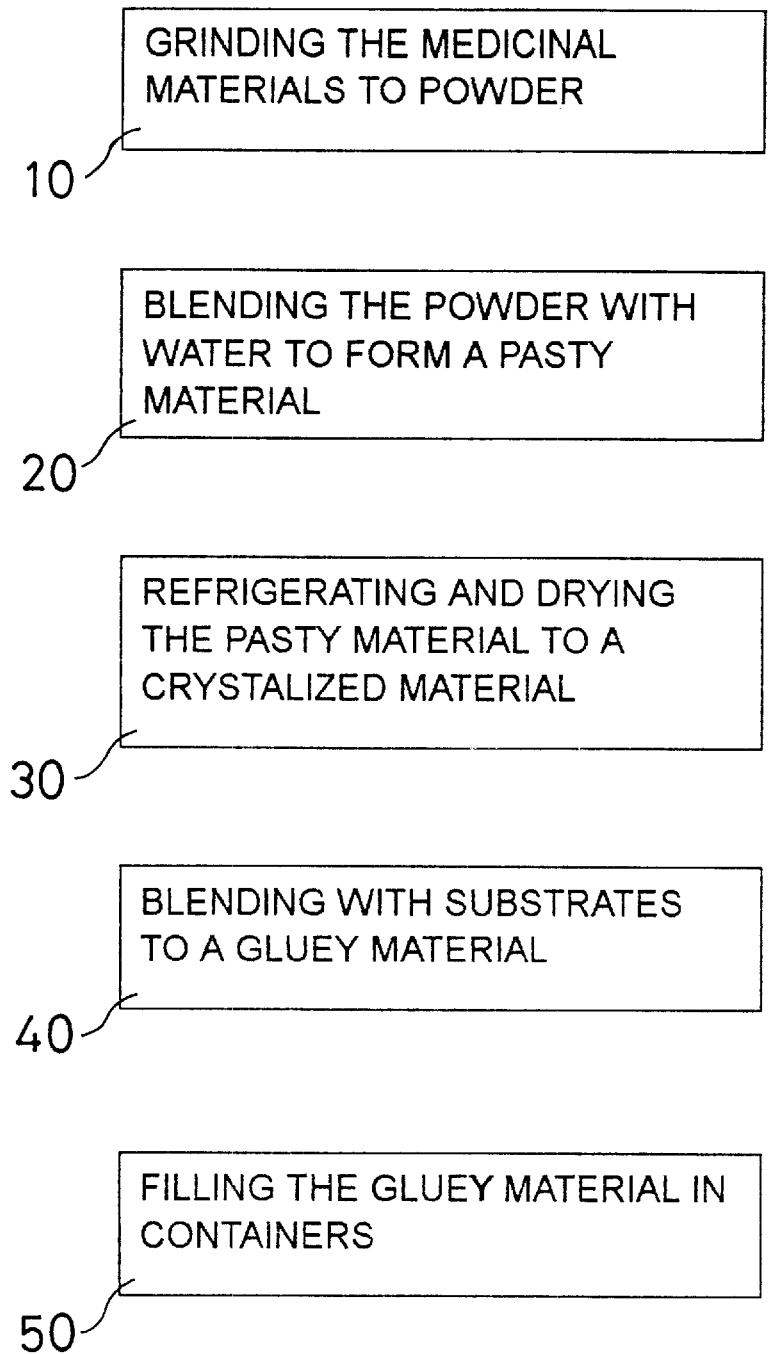
FIG. 1 is a block diagram illustrating the procedures for manufacturing a medicinal preparation in accordance with the present invention.

Referring to the drawing, illustrated are the procedures for manufacturing a medicinal preparation in accordance with the present invention. First, a number of medicinal materials are required to be prepared, and may be used for moistening, nourishing, disinfecting, sterilizing, or for decreasing inflammation or the like. The medicinal materials include asari radix having about 10–30% by weight, *fructus cnidii* having about 10–30% by weight, *nelumbo nucifera gaertner* having about 5–10% by weight, *ginseng radix* having about 3–5% by weight, *angelica sinensis radix* having about 5–10% by weight, *scutellaria baicalensis* having about 5–10% by weight, *phellodendron amurense radix* having about 5–10% by weight, *evodiae fructus* having about 10–30% by weight, and *saussureae radix* having about 10–30% by weight.

The medicinal materials are medicinal herbs and are grounded into powder or particles each having about 120 milligrams, or the like, in the process 10 as shown in FIG. 1. The powder is then blended with water or the other fluid, in order to form a pasty material, in the process 20 as shown in FIG. 1, for allowing the powder of the various medicinal herbs or materials to be suitably or well mixed or blended with each other. The pasty material is then subjected to a refrigerating and drying process 30 (FIG. 1) in order to dry the pasty material or to remove the water from the pasty material, and in order to decrease the temperature of the pasty material to about 10° C. below zero degrees, or to refrigerate the pasty material into a crystallized material.

A number of substrates are then prepared and include papaya enzyme having about 10% by weight, aloe jelly having about 10% by weight, bulbus lilii having about 0.5% by weight, glycerine having about 15% by weight, almond oil having about 15% by weight, ginsengperfume having about 0.5% by weight, fatty acid having about 5% by weight, lactic acid having about 0.1% by weight, distillation water or the typical water having about 23.9% by weight, and carbomer having about 20% by weight. The substrates are then mixed or blended with the crystallized material, and are rotated for a predetermined term of time, such as 20 minutes, and are rotated with a rotational speed of about 1500 rps, for allowing the substrates and the crystallized material to be suitably or uniformly mixed or blended with each other, and in order to form a sticky or gummy or gluey material in the process 40. The substrates may also be directly mixed with the pasty material, instead of the crystallized material.

The gluey material may then be filled into containers or envelopes or capsules in process 50 (FIG. 1) for being used by the users. For example, the medicinal preparation may be filled into the capsules and may then be taken orally, or may be directly applied onto the vaginas of the users, or the like. It is to be noted that the medicinal materials or the medicinal herbs are primarily used for medical use. The substrates maybe selectively or optionally included or added into the medicinal materials or the medicinal herbs, but not necessarily be included or added into the medicinal materials or the medicinal herbs. The medicinal preparation thus prepared include a number of medicinal herbs or materials that may be used for moistening, nourishing, disinfecting, sterilizing, or for decreasing inflammation or the like, such that the medicinal preparation may be used for moistening and tightening the vaginas of women or for increasing or recovering the resilience of the muscles of the vaginas of the women, or may be used for disinfecting the vaginas of women, in order to remove the bad odors, inflammation, leucorrhoea or the like from the vaginas of women, or may be used for cleaning and moistening the vaginas of women, for avoiding the vaginas infectious problems, and for hygienic use.

Accordingly, the medicinal preparation in accordance with the present invention may be used for moistening and tightening the vaginas of women, for increasing or recovering the resilience of the muscles of the vaginas of the women, or for disinfecting the vaginas of women, in order to remove the bad odors, inflammation, leucorrhoea or the like from the vaginas of women, or for cleaning and moistening the vaginas of women, for avoiding the vaginas infectious problems.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A medicinal preparation comprising:
    a plurality of medicinal materials including *asari radix, fructus cnidii, nelumbo nucifera gaertner, ginseng radix, angelica sinensis radix, scutellaria baicalensis, phellodendron amurense radix, evodiae fructus*, and *saussureae radix*, said medicinal materials being grounded into powder, and
    water blending with said powder of said medicinal materials to form a pasty material.

2. The medicinal preparation according to claim 1, wherein said *asari radix* includes 10–30% by weight, said *fructus cnidii* includes 10–30% by weight, said *nelumbo nucifera gaertner* includes 5–10% by weight, said *ginseng radix* includes 3–5% by weight, said *angelica sinensis radix* includes 5–10% by weight, said *scutellaria baicalensis* includes 5–10% by weight, said *phellodendron amurense radix* includes 5–10% by weight, said *evodiae fructus* includes 10–30% by weight, and said *saussureae radix* includes 10–30% by weight.

3. The medicinal preparation according to claim 1 further comprising a plurality of substrates mixed with said pasty material, said substrates including papaya enzyme, aloe jelly, bulbus lilii, glycerine, almond oil, ginsengperfume, fatty acid, lactic acid, carbomer, and water material.

4. The medicinal preparation according to claim 3, wherein said papaya enzyme includes 10% by weight, said aloe jelly includes 10% by weight, said bulbus lilii includes 0.5% by weight, said glycerine includes 15% by weight, said almond oil includes 15% by weight, said ginsengperfume includes 0.5% by weight, said fatty acid includes 5% by weight, said lactic acid includes 0.1% by weight, said carbomer includes 20% by weight, and said water material includes 23.9% by weight.

5. The medicinal preparation according to claim 3, wherein said substrates and said pasty material are rotated with a rotational speed of 1500 rps for well mixing said substrates and said pasty material to form a gluey material.

6. The medicinal preparation according to claim 1, wherein said pasty material is refrigerated and dried to remove water from said pasty material and to refrigerate said pasty material to a crystallized material.

7. The medicinal preparation according to claim 6 further comprising a plurality of substrates mixed with said crystallized material, said substrates including papaya enzyme, aloe jelly, bulbus lilii, glycerine, almond oil, ginsengperfume, fatty acid, lactic acid, carbomer, and water material.

8. The medicinal preparation according to claim 7, wherein said papaya enzyme includes 10% by weight, said aloe jelly includes 10% by weight, said bulbus lilii includes 0.5% by weight, said glycerine includes 15% by weight, said almond oil includes 15% by weight, said ginsengperfume includes 0.5% by weight, said fatty acid includes 5% by weight, said lactic acid includes 0.1% by weight, said carbomer includes 20% by weight, and said water material includes 23.9% by weight.

9. The medicinal preparation according to claim 7, wherein said substrates and said crystallized material are rotated with a rotational speed of 1500 rps for well mixing said substrates and said crystallized material to form a gluey material.

* * * * *